United States Patent
Budd et al.

(10) Patent No.: US 7,754,746 B2
(45) Date of Patent: Jul. 13, 2010

(54) ORGANIC COMPOUNDS

(75) Inventors: Emma Budd, Horsham (GB); Julia Doris Ida Hatto, Horsham (GB); Judy Fox Hayler, Horsham (GB); Darren Mark Legrand, Horsham (GB); Barbara Valade, Senago (IT)

(73) Assignee: Novartis AG, Basel (CH)

( * ) Notice: Subject to any disclaimer, the term of this patent is extended or adjusted under 35 U.S.C. 154(b) by 120 days.

(21) Appl. No.: 12/097,723

(22) PCT Filed: Dec. 13, 2006

(86) PCT No.: PCT/EP2006/012018

§ 371 (c)(1),
(2), (4) Date: Jun. 16, 2008

(87) PCT Pub. No.: WO2007/068473

PCT Pub. Date: Jun. 21, 2007

(65) Prior Publication Data

US 2008/0319033 A1    Dec. 25, 2008

(30) Foreign Application Priority Data

Dec. 16, 2005  (GB) ................. 0525671.4

(51) Int. Cl.
*C07D 413/12* (2006.01)
*C07D 411/12* (2006.01)
*C07D 277/48* (2006.01)
*A61K 31/427* (2006.01)
*A61K 31/426* (2006.01)

(52) U.S. Cl. ...................... 514/371; 548/196

(58) Field of Classification Search ................. 514/371; 548/196

See application file for complete search history.

(56) References Cited

U.S. PATENT DOCUMENTS

2008/0280871 A1 * 11/2008 Bloomfield et al. .... 514/210.18

FOREIGN PATENT DOCUMENTS

| WO | WO03/072557 A1 | 9/2003 |
| WO | WO 03072557 A1 * | 9/2003 |
| WO | WO2005/021519 A2 | 3/2005 |

* cited by examiner

*Primary Examiner*—Rebecca L Anderson
*Assistant Examiner*—Matthew P Coughlin
(74) *Attorney, Agent, or Firm*—Paul D. Strain, Esq.; Fanelli Strain & Haag PLLC

(57) ABSTRACT

Compounds of formula I

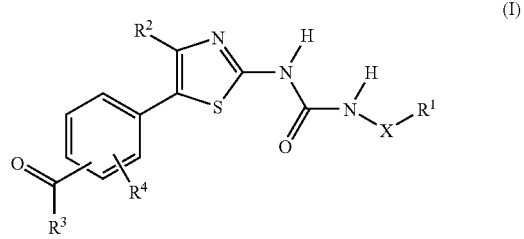

in free or salt form, wherein $R^1$, $R^2$, $R^3$, $R^4$ and X have the meanings as indicated in the specification, are useful for treating diseases mediated by phosphatidylinositol 3-kinase. Pharmaceutical compositions that contain the compounds and processes for preparing the compounds are also described.

9 Claims, No Drawings

ORGANIC COMPOUNDS

This application is a U.S. National Phase filing of PCT/EP2006/012018 filed 13 Dec. 2006, and claims priority to GB Patent Application 0525671.4 filed 16 Dec. 2005, the contents of which are incorporated herein by reference in their entirety.

The present invention relates to organic compounds, their preparation and their use as pharmaceuticals.

In a first aspect, the present invention provides compounds of formula I

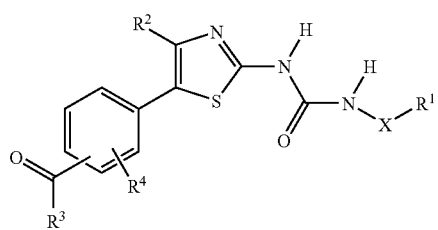

in free or salt form, wherein:

$R^1$ is $C_1$-$C_6$-alkylaminocarbonyl, where the alkyl is optionally substituted by one or more halo, hydroxyl or $C_1$-$C_6$-alkoxy groups, or $R^1$ is a 5- or 6-membered heteroaromatic ring having one or more ring heteroatoms selected from the group consisting of oxygen, nitrogen and sulphur, said ring being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

$R^2$ is $C_1$-$C_3$-alkyl;

$R^3$ is $C_1$-$C_6$-alkyl, $C_3$-$C_6$-cycloalkyl, —$NR^5R^6$ or —$OR^7$, where said alkyl and cycloalkyl groups are optionally substituted by one or more halo, hydroxyl or $C_1$-$C_6$-alkoxy groups and said cycloalkyl group is optionally further substituted by $C_1$-$C_6$-alkyl;

$R^4$ is one or more optional phenyl substituents independently selected from halo, $C_1$-$C_6$-alkyl, hydroxyl or $C_1$-$C_6$-alkoxy, where said alkyl and alkoxy groups are optionally further substituted by one or more halo, hydroxyl and $C_1$-$C_6$-alkoxy groups; or $R^3$ and $R^4$ together form a fused 5-7 membered cycloalkanone ring;

$R^5$ and $R^6$ independently represent hydrogen, $C_1$-$C_6$-alkyl, $C_3$-$C_6$-cycloalkyl, hydroxyl or $C_1$-$C_6$-alkoxy, where said alkyl, alkoxy and cycloalkyl groups are optionally substituted by one or more halo, hydroxyl or $C_1$-$C_6$-alkoxy groups and said cycloalkyl group is optionally further substituted by $C_1$-$C_6$-alkyl;

$R^7$ is hydrogen, $C_1$-$C_6$-alkyl or $C_3$-$C_6$-cycloalkyl, where said alkyl and cycloalkyl groups are optionally substituted by one or more halo, hydroxyl or $C_1$-$C_6$-alkoxy groups and said cycloalkyl group is optionally further substituted by $C_1$-$C_6$-alkyl;

X is —$CH_2$—$C(R^8)R^9$;

$R^8$ and $R^9$ are independently selected from hydrogen, halo, hydroxy and $C_1$-$C_6$-alkyl where said alkyl group is optionally substituted by one or more halo, hydroxyl or $C_1$-$C_6$-alkoxy groups; and The group $C(O)R^3$ is located at the 3- or 4-position on the phenyl ring.

Terms used in the specification have the following meanings:

"$C_1$-$C_6$-alkyl" denotes a straight chain or branched alkyl group comprising 1 to 6 carbons, which may be, for example, methyl, ethyl, n-propyl, isopropyl, n-butyl, isobutyl, sec-butyl, tert-butyl, straight or branched pentyl, straight or branched hexyl.

"$C_3$-$C_6$-cycloalkyl" denotes a fully saturated carbocyclic ring having 3 to 6 ring carbon atoms, for example a monocyclic group such as a cyclopropyl, cyclobutyl, cyclopentyl or cyclohexyl.

"$C_1$-$C_6$-alkoxy" denotes a straight chain or branched alkyl chain linked to O, which may be, for example, methoxy, ethoxy, n-propoxy, isopropoxy, n-butoxy, isobutoxy, sec-butoxy, tert-butoxy, straight or branched pentoxy, straight or branched hexyloxy.

"$C_1$-$C_6$-alkylcarbonyl", "$C_1$-$C_8$-alkoxycarbonyl" and "$C_1$-$C_8$-haloalkylcarbonyl" and denote $C_1$-$C_8$-alkyl, $C_1$-$C_8$-alkoxy or $C_1$-$C_8$-haloalkyl respectively as hereinbefore defined attached by a carbon atom to a carbonyl group.

"5- or 6-membered heteroaromatic ring containing at least one ring heteroatom selected from the group consisting of nitrogen, oxygen and sulphur" as used herein may be, for example, furan, pyrrole, pyrazole, imidazole, triazole, isotriazole, tetrazole, thiadiazole, isothiazole, oxadiazole, pyridine, oxazole, isoxazole, pyrazine, pyridazine, pyrimidine, triazine or thiazole.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

According to formula (I), the following suitable, preferred, more preferred or most preferred aspects of the invention may be incorporated independently, collectively or in any combination.

Preferably, the group $C(O)R^3$ is located at the 4-position on the phenyl ring.

Where $R^1$ is optionally substituted $C_1$-$C_6$-alkylaminocarbonyl, the alkyl is suitably ethyl or tert-butyl, optionally substituted by one or more, preferably one to three, halo, suitably fluoro. Where $R^1$ is $C_1$-$C_6$-alkylaminocarbonyl, $R^1$ is most suitably tert-butyl-, 2-fluoroethyl-2,2-difluoroethyl- or 2,2,2-trifluoroethyl-aminocarbonyl.

Where $R^1$ is an optionally substituted 5- or 6-membered heteroaromatic ring having one or more ring heteroatoms selected from the group consisting of oxygen, nitrogen and sulphur, $R^1$ is suitably optionally substituted imidazolyl, e.g. imidazo-4-yl, tetrazolyl, e.g. 2H-tetrazol-5-yl or oxazolyl, e.g. oxazol-2-yl, where optionally substituents are suitably $C_1$-$C_6$-alkyl, e.g. ethyl or isopropyl, where said alkyl is suitably optionally substituted by halo, e.g. fluoro. Where $R^1$ is an optionally substituted 5- or 6-membered heteroaromatic ring, $R^1$ is preferably imidazo-4-yl, 2H-tetrazol-5-yl or oxazol-2-yl substituted by ethyl, isopropyl or 2-fluoroethyl.

$R^2$ is preferably methyl.

Where $R^3$ is —$NR^5R^6$, suitably $R^5$ is hydrogen or $C_1$-$C_6$-alkyl, e.g. methyl, and $R^6$ is $C_1$-$C_6$-alkyl, e.g. methyl or isopropyl, $C_3$-$C_6$-cycloalkyl, e.g. cyclopropyl, or $C_1$-$C_6$-alkoxy, e.g. methoxy.

Where $R^3$ is —$OR^7$, $R^7$ is suitably hydrogen or $C_1$-$C_6$-alkyl, e.g. methyl, ethyl.

$R^3$ is suitably $C_1$-$C_6$-alkyl, e.g. methyl or ethyl, $C_3$-$C_6$-cycloalkyl, e.g. cyclopropyl, —$NR^5R^6$, e.g. methylamino, ethylamino or cyclopropylamino, or —OR$^7$, e.g. hydroxyl or methoxy. R$^3$ is preferably C$_1$-C$_6$-alkyl.

Where the phenyl is further substituted, R$^4$ is suitably a single substituent, more suitably a phenyl 3-substituent. R$^4$ is suitably halo, e.g. fluoro, preferably in the 3-position.

Where R$^3$ and R$^4$ together form a fused 5-7 membered cycloakanone ring, the bicyclic ring formed with the phenyl is suitably a 1-oxo-indan-5-yl group.

X is preferably ethylene, i.e. R$^8$ and R$^9$ are hydrogen.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

Specific preferred compounds of formula I are described hereinafter in the Examples.

The invention provides, in another aspect, a process for preparing a compound of formula I in free or salt form.

According to a first process (A), a compound of formula (I) may be prepared by reaction of a compound of formula (II) with a compound of formula (III)

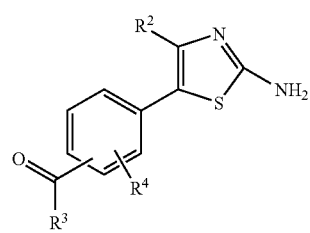
(II)

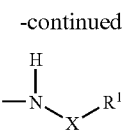
(III)

by reaction with carbonyldiimidazole in a suitable solvent, as described in WO05/21519.

Compounds of formula (II) may be prepared by methods described in WO05/21519. Compounds of formula (II) may also be prepared by reaction of compounds of formula (IV) and (V)

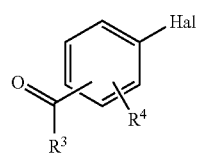
(IV)

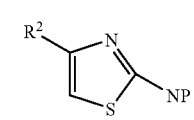
(V)

where P is a suitable nitrogen protecting group, such as acetyl, by reaction with a palladium catalyst, such as Pd(t-Bu)$_3$, in the presence of a base, such as caesium carbonate, in a suitable solvent, such as dimethylformamide, at elevated temperature, followed by removal of the protecting group P, under standard conditions.

Compounds of formula (II) may also be prepared by reaction of compounds of formula (VI) and (VII)

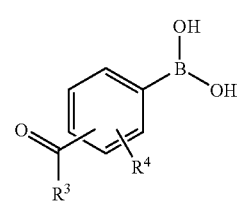
(VI)

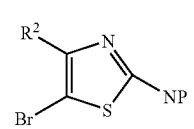
(VII)

where P is a suitable nitrogen protecting group, such as to form a benzhydrylidene, by reaction with a palladium catalyst, such as terakis triphenyl phosphine palladium (0), in the presence of a base, such as caesium carbonate, in a suitable solvent, such as dioxane/water, at elevated temperature, followed by removal of the protecting group P, under standard conditions.

Compounds of formula (III) may be prepared by methods described in WO05/21519.

Compounds of formula (III), where X is ethylene and R$^1$ is substituted tetrazolyl, may be prepared by the method described in scheme 1 below, where R is a suitably substituent according to formula (I) and P is a suitable N-protecting group, such as t-Boc:

Scheme 1

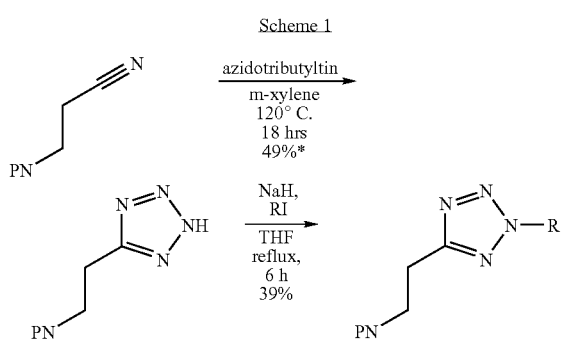

followed by removal of the N-protecting group under standard conditions.

Compounds of formula (III), where X is ethylene and R¹ is 1-substituted imidazolyl, may be prepared by methods described in WO05/21519 or may be prepared by the methods described in the following scheme 2, where R is a suitable substituent as described in formula (I):

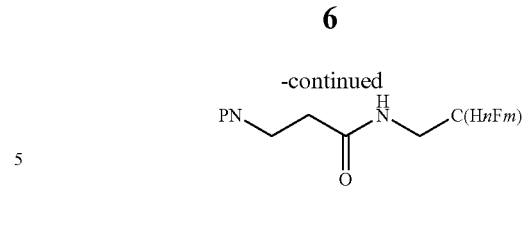

Where n = 0, 1, 2 & m = 1, 2, 3 followed by removal of the N-protecting group under standard conditions. It will be understood that compounds of formula (I) may be used to prepare other compounds of formula (I), for example derivatisation of compounds where R³ represents NH$_2$ or OH, by methods well known in the art.

Compounds of formula (IV), (V), (VI) and (VII) are known or may be prepared by methods described hereinafter or which are described in the art and/or which are well-known to those skilled in the art.

Compounds of formula I in free form may be converted into salt form, and vice versa, in a conventional manner. The

Scheme 2

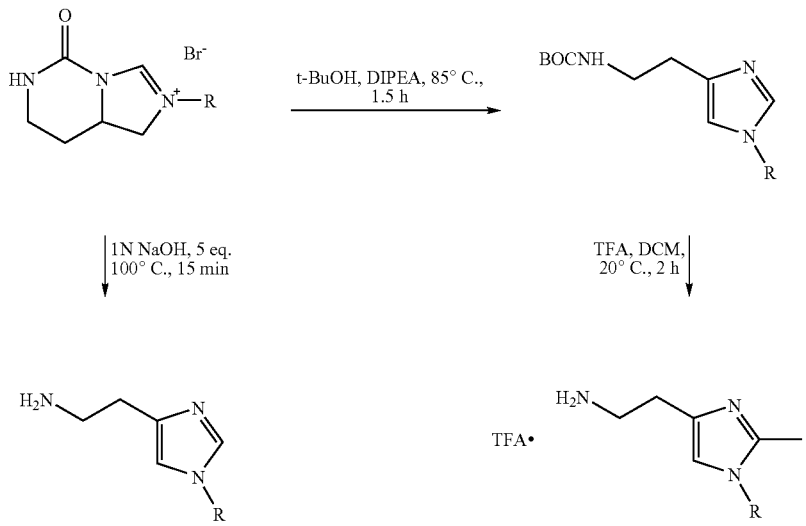

Compounds of formula (III), where X is ethylene and R¹ is C$_1$-C$_6$-alkylaminocarbonyl substituted by one or more fluoro groups may be prepared by methods described according to the following scheme 3, where P is suitable N-protecting group, such as t-Boc:

Scheme 3

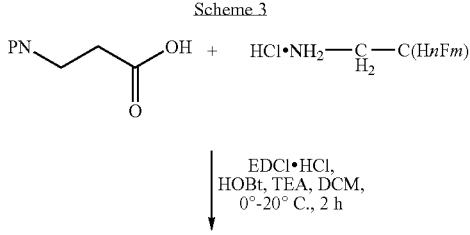

compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I and their pharmaceutically acceptable salts, hereinafter referred to alternatively as agents of the invention, are useful as pharmaceuticals. In particular, they exhibit inhibition of phosphatidylinositol 3-kinase (Pi3 kinase) enzymes, especially the gamma isoform (p110γ), which are responsible for generating phosphorylated signalling products. The inhibitory properties of compounds of formula I may be demonstrated in the following test procedures:

Baculovirus expressing different fragments of PI3Kγ fused to GST have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.,* 324:489. Residues 38-1102 of human PI3Kγ are subcloned into the BamH1 and EcoR1 sites of the transfer vector pAcG2T (Pharmingen) to create a GST-PI3Kγ lacking the first 37 residues of PI3Kγ. To express the recombinant protein, Sf9 (*Spodoptera frugiperda* 9) insect cells are routinely maintained at densities between $3\times10^5$ and $3\times10^6$ cells/ml in serum containing TNMFH medium (Sigma). Sf9 cells, at a density of $2\times10^6$ are infected with human GST-PI3KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1\times10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 µl test compound in 5% dimethylsulphoxide and 20 µl assay mix (40 mM Tris, 200 mM NaCl, 2 mM ethyleneglycol-aminoethyl-tetraacetic acid (EGTA), 15 µg/ml phosphatidylinositol, 12.5 µM adenosine triphosphate (ATP), 25 mM $MgCl_2$, 0.1 µCi [$^{33}$P]ATP). The reaction is started by the addition of 20 µl of enzyme mix (40 mM Tris, 200 mM NaCl, 2 mM EGTA containing recombinant GST-p110γ). The plate is incubated at room temperature for 60 minutes and the reaction terminated by the adding 150 µl of WGA-bead stop solution (40 mM Tris, 200 mM NaCl, 2 mM EGTA, 1.3 mM ethylene diamine tetraacetic acid (EDTA), 2.6 µM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 µl of 5% dimethylsulphoxide (DMSO) and non-specific activity is determined by adding 10 µl 50 mM EDTA in place of the test compound.

Compounds of the Examples hereinbelow have $IC_{50}$ values below 0.75 µM in the aforementioned assay. For example the compounds of Examples 1, 5 and 27 have $IC_{50}$ values of 0.1, 0.11 and 0.09 µM respectively.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the Pi3 kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include septic shock, rheumatoid arthritis, osteoarthritis, proliferative diseases such as cancer, athersclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49-57; Renzi et al, Am. Rev. Respir. Dis. (1993) 148:932-939; Tsuyuki et al., J. Clin. Invest. (1995) 96:2924-2931; and Cernadas et al (1999) Am. J. Respir. Cell Mol. Biol. 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®-AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma) and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially a compound of formula

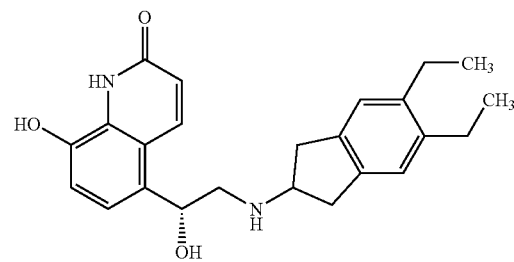

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), and WO 00/66559 (particularly claim 9).

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/ or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

EXAMPLES

Compounds of formula I are shown in the Table 1 below, their method of preparation being described thereafter. The table also shows mass spectrometry (MH+) data. The examples are in free form.

TABLE 1

| Ex. | Ar | R¹ | M/s MH+ |
|---|---|---|---|
| 1 | 4-acetyl-phenyl (H₃C-C(=O)-C₆H₄-) | -CH₂CH₂-C(=O)-NH-C(CH₃)₃ | 403.1 |
| 2 | 4-acetyl-phenyl (H₃C-C(=O)-C₆H₄-) | -CH₂CH₂-C(=O)-NH-CH₂CH₂F | 393.16 |
| 3 | 4-acetyl-phenyl (H₃C-C(=O)-C₆H₄-) | -CH₂CH₂-C(=O)-NH-CH₂CHF₂ | 411.13 |

TABLE 1-continued
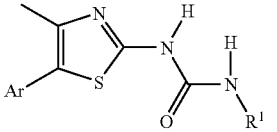
(X)
| | Ar | R¹ | |
|---|---|---|---|
| 4 | 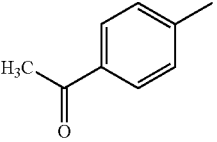 | 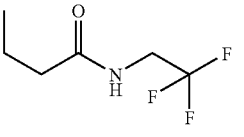 | 429.12 |
| 5 | 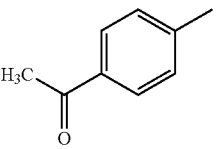 | 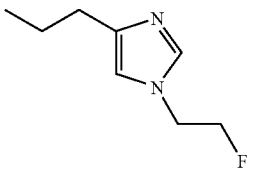 | 416.13 |
| 6 | 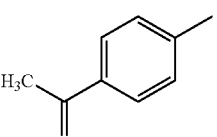 | 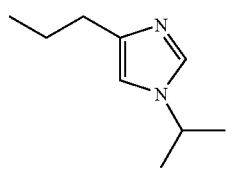 | 412.45 |
| 7 | 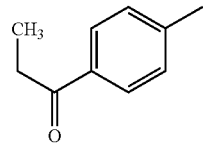 | 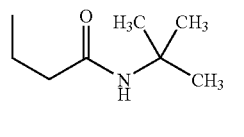 | 417.52 |
| 8 | 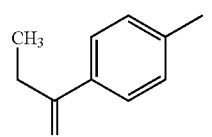 | 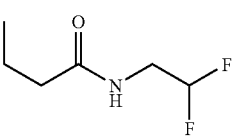 | 425.48 |
| 9 | 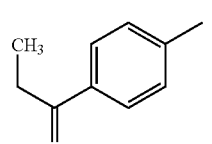 | 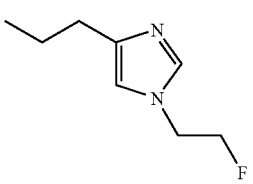 | 430.50 |
| 10 | 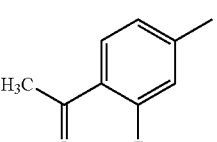 | 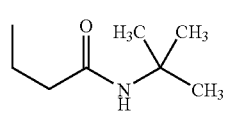 | 421.44 |
| 11 | 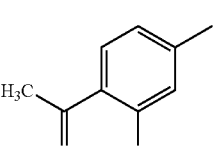 | 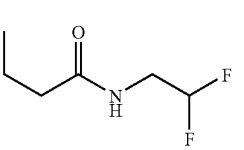 | 429.42 |

TABLE 1-continued (X) structure: 4-methylthiazole with Ar at 5-position, connected via NH-C(O)-NH-R¹

| # | Ar | R¹ | MW |
|---|----|----|-----|
| 12 | 4-acetyl-3-fluorophenyl (H₃C-C(O)-C₆H₃(F)-) | 1-isopropyl-4-propyl-imidazol-yl | 430.43 |
| 13 | 5-(1-oxo-indan-yl) | N-(2,2-difluoroethyl)butanamide | 423.29 |
| 14 | 5-(1-oxo-indan-yl) | 1-(2-fluoroethyl)-4-propyl-imidazol-yl | 428.20 |
| 15 | 5-(1-oxo-indan-yl) | 1-isopropyl-4-propyl-imidazol-yl | 424.10 |
| 16 | 4-(cyclopropylcarbonyl)phenyl | N-tert-butyl-butanamide | 429.20 |
| 17 | 4-(cyclopropylcarbonyl)phenyl | N-(2,2-difluoroethyl)butanamide | 437.14 |
| 18 | 4-(cyclopropylcarbonyl)phenyl | 1-isopropyl-4-propyl-imidazol-yl | 438.23 |
| 19 | 4-(cyclopropylcarbonyl)phenyl | 1-ethyl-4-propyl-imidazol-yl | 424.25 |

TABLE 1-continued
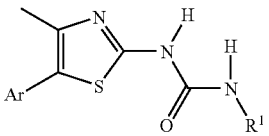
(X)
| Ex. | Ar | Rb | M/s MH+ |
|---|---|---|---|
| 20 | 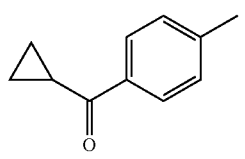 | 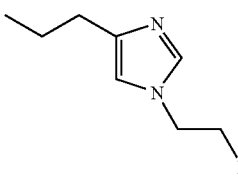 | 442.19 |
| 21 | 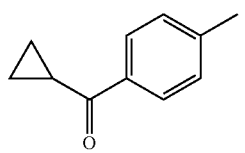 | 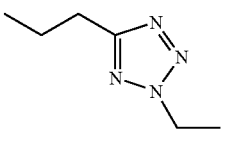 | 426.20 |
| 22 | 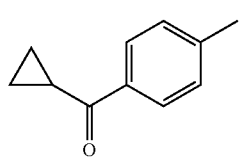 | 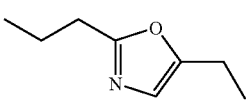 | 425.2 |
| Ex. | Ar | Rb | M/s MH+ |
|---|---|---|---|
| 23 | 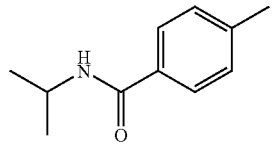 | 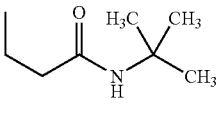 | 446.46 |
| 24 | 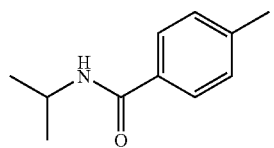 | 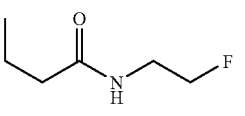 | — |
| 25 | 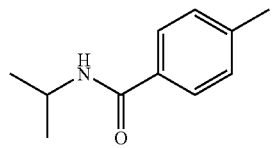 | 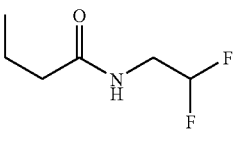 | — |
| 26 | 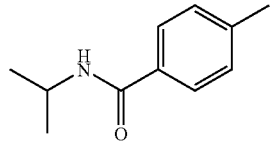 | 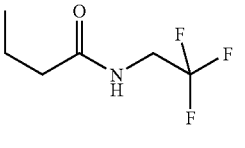 | — |
| 27 | 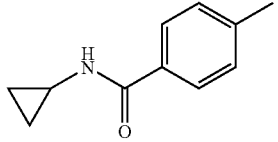 | 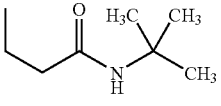 | 444.47 |

TABLE 1-continued

Structure (X):

| # | Ar | R¹ | MS |
|---|----|----|-----|
| 28 | 4-methylphenyl-C(O)NH-cyclopropyl | -CH₂CH₂C(O)NH-CH₂CH₂F | — |
| 29 | 4-methylphenyl-C(O)NH-cyclopropyl | -CH₂CH₂C(O)NH-CH₂CHF₂ | — |
| 30 | 4-methylphenyl-C(O)NH-cyclopropyl | -CH₂CH₂C(O)NH-CH₂CF₃ | — |
| 31 | 4-methylphenyl-C(O)NHCH₃ | -CH₂CH₂C(O)NH-C(CH₃)₃ | 418.18 |
| 32 | 4-methylphenyl-C(O)NHCH₃ | -CH₂CH₂C(O)NH-CH₂CHF₂ | 426.15 |
| 33 | 3-methylphenyl-C(O)NH-cyclopropyl | -CH₂CH₂C(O)NH-CH₂CHF₂ | 452.27 |
| 34 | 3-methylphenyl-C(O)NH-cyclopropyl | 1-(2-fluoroethyl)-4-propyl-imidazolyl | 457.29 |
| 35 | 4-methylphenyl-C(O)OCH₃ | -CH₂CH₂C(O)NH-CH₂CHF₂ | — |

TABLE 1-continued (X) structure: Ar-substituted 4-methyl-thiazol-2-yl urea with R¹

| # | Ar | R¹ | |
|---|---|---|---|
| 36 | methyl 4-methylbenzoate | 1-isopropyl-4-propyl-imidazole | — |
| 37 | methyl 4-methylbenzoate | 1-(2-fluoroethyl)-4-propyl-imidazole | — |
| 38 | ethyl 4-methylbenzoate | N-(2,2-difluoroethyl)butyramide | — |
| 39 | ethyl 4-methylbenzoate | 1-(2-fluoroethyl)-4-propyl-imidazole | — |
| 40 | 4-methylbenzoic acid | N-(2,2-difluoroethyl)butyramide | — |
| 41 | 4-methylbenzoic acid | 1-isopropyl-4-propyl-imidazole | — |
| 42 | 4-methylbenzoic acid | 1-(2-fluoroethyl)-4-propyl-imidazole | — |

TABLE 1-continued

| | | | (X) |
|---|---|---|---|
| 43 | ![structure] | ![structure] | 448.28 |
| 44 | ![structure] | ![structure] | 457.29 |
| 45 | ![structure] | ![structure] | 461.26 |

Preparation of Specific Examples

Abbreviations used are as follows: BOC is t-butoxycarbonyl, DCM is dichloromethane, DIPEA is diisopropylethylamine DME is dimethoxyethane, DMF is dimethylformamide, EDCI is 1-ethyl-3-(3-dimethylaminopropyl)carbodiimide, HATU is O-(7-azabenzotriazol-1-yl)-N,N,—N',N'-tetramethyl-uronium hexafluorophophate, HOBt is 4-hydroxybenzotriazole, NBS is N-bromosuccinimide, RT is room temperature and THF is tetrahydrofuran.

The examples described above may be prepared according to the procedures described generally and specifically in WO05/21519. The following example is indicative of the preparation of compounds of formula (I)

Example 1a

Imidazole-1-carboxylic acid [5-(4-acetyl-phenyl)-4-methyl-thiazol-2-yl]-amide

A solution of 1-[4-(2-Amino-4-methyl-thiazol-5-yl)-phenyl]-ethanone (0.57 g, 2.45 mmol) is dissolved in a mixture of THF (10 ml) and dichloromethane (20 ml) and heated in an oil bath set to 50° C. Carbonyldiimidazole is added (0.64 g, 3.92 mmol) and the reaction mixture heated at 50° C. for a further 2 hours in which a pale yellow precipitate forms. After cooling to room temperature the precipitate is filtered, washed with dichloromethane and dried under high vacuum.

Example 1b

3-{3-[5-(4-Acetyl-phenyl)-4-methyl-thiazol-2-yl]-ureido}-N-tert-butyl-propionamide Imidazole-1-carboxylic acid [5-(4-acetyl-phenyl)-4-methyl-thiazol-2-yl]-amide (0.455 g, 1.40 mmol) is dissolved in dimethylformamide (10 ml) and treated with triethylamine (0.21 ml, 1.47 mmol) and 3-Amino-N-tert-butyl-propionamide (0.266 g, 1.47 mmol). The reaction mixture is stirred for 1.5 hours, then water (200 ml) added and the resulting suspension filtered. The solid is washed with water and dried under high vacuum to afford the titled product as a pale yellow solid. [M+H] 403.34

Intermediates 1

The following syntheses are representative of the 'Suzuki' pathway to the compounds of formula (I) via intermediates of formula (II):

Intermediate 1a

Benzhydrylidene-(4-methyl-thiazol-2-yl)-amine

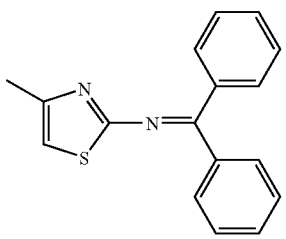

Benzophenone imine (39.8 g, 0.22 mol) is added to a solution of 2-Amino-4-methyl-1,3-thiazole (30 g, 0.261) in toluene (450 ml) and heated at reflux under an inert atmosphere for 18 h. The mixture is cooled to room temperature and washed with citrate buffer (2×250 ml), water (2×250 ml), brine (2×250 ml), dried (MgSO$_4$ and decolourising charcoal), filtered and evaporated to an orange solid (42.9 g, 70%).

Intermediate 1b

Benzhydrylidene-(5-bromo-4-methyl-thaizol-2-yl)-amine

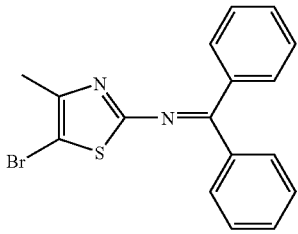

N-Bromosuccimide (26.8 g, 0.15 mol) is added to a solution of benzhydrylidene-(4-methyl-thiazol-2-yl)-amine (41.9 g, 0.15 mol) in glacial acetic acid (200 ml) and stirred for 1.25 h. The solid is filtered off and dried in vacuo. This is dissolved in dicholoromethane (400 ml) and washed with sodium bicarbonate solution (2×400 ml), water (2×400 ml), brine (2×400 ml), dried (MgSO$_4$), filtered and evaporated to yield a yellow solid which is dried in vacuo (39.3 g, 74%).

Intermediate 1c

1-{4-[Benzhydrylidene-amino]-4-methyl-thiazol-5-yl}-phenyl}-ethanone

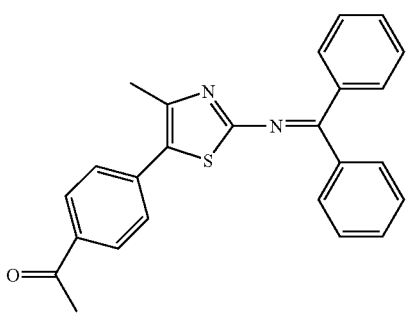

4-Acetylphenyl boronic acid (1.8 g, 0.01 μmol, 1.1 eq), tetrakistriphenylphosphine palladium(0) (0.7 g, 0.6 mmol), caesium carbonate (9.8 g, 0.03 mol) in water (10 ml), are added to a solution of benzhydrylidene-(5-bromo-4-methyl-thiazol-2-yl)-amine (3.5 g, 0.01 mol) in dioxane (80 ml) and heated at reflux for 6 h. The solvent is removed in vacuo, to yield an oily suspension which is partitioned between dichloromethane (75 ml) and sat. sodium bicarbonate (75 ml). The layers are separated and the organics washed with water (75 ml) and brine (75 ml), dried (MgSO$_4$ and charcoal), filtered and evaporated to a brown solid (4.0 g).

Intermediate 1d

1-[4-(2-Amino-4-methyl-thiazol-5-yl)-phenyl]-ethanone

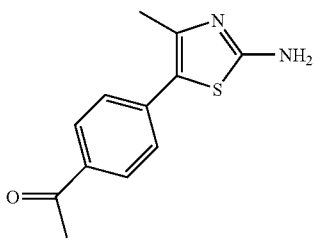

2M hydrochloric acid (45 ml) is added to 1-{4-[benzhydrylidene-amino]-4-methyl-thiazol-5-yl}-phenyl}-ethanone (4.0 g, 0.01 mol) in THF (175 ml) and stirred for 1 h. The mixture is partitioned between 0.5M hydrochloric acid (50 ml), iso-hexane (100 ml) and ethyl acetate (50 ml). The aqueous phase was basified with 4M sodium hydroxide (30 ml) and extracted with dichloromethane (2×100 ml). The organics were dried (MgSO$_4$), filtered and evaporated to a yellow solid (1.9 g, 82%).

Intermediates 2

The following syntheses are representative of the 'Heck' pathway to the compounds of formula (I) via intermediates of formula (IV):

Intermediate 2a

N-[5-(4-Cyclopropanecarbonyl-phenyl)-4-methyl-thiazol-2-yl]-acetamide

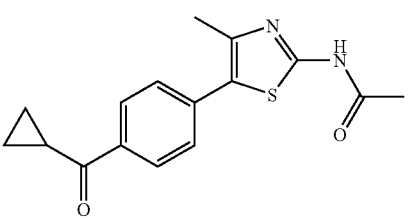

Dry, degassed DMF (90 ml) was added to 4-chlorophenyl-cyclopropyl ketone (5.0 g, 27.6 mmol), N-(4-Methyl-thiazol-2-yl)-acetamide (3.6 g, 23.1 mmol), Bis(tri-t-butylphosphine) palladium (0) (1.18 g, 2.31 mmol) and caesium carbonate (15.03 g, 46.1 mmol), and the reaction mixture heated to 150° C. for 4 hours. The reaction mixture was filtered through celite and the filtrate reduced in vacuo. The material was purified by column chromatography using as eluant 2:1 to 1:2 Iso-hexane:EtOAc gradient. (M+H) 259.0.

Intermediate 2b

[4-(2-Amino-4-methyl-thiazol-5-yl)-phenyl]-cyclopropyl-methanone

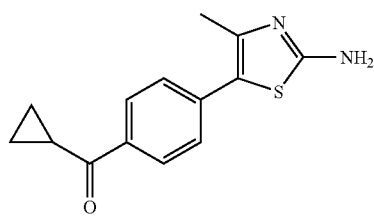

Ethanol (34 ml) and 6M NaOH (18.6 ml, 113.2 mmol) were added to N-[5-(4-Cyclopropanecarbonyl-phenyl)-4-methyl-thiazol-2-yl]-acetamide (3.4 g, 11.32 mmol). The reaction mixture was heated to 85° C. for 5.5 hours, after which further NaOH (3.72 ml, 22.64 mmol) was added and heating continues for 1.5 hours. The resulting precipitate was isolated by vacuum filtration. (M+H) 301.26.

Intermediate 2c

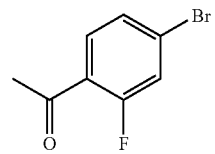

Ref: WO2003095441

Intermediates 3

The following syntheses are representative of the 3 fluoro-containing amines intermediates as described in Scheme 3:

Intermediate 3a

[2-(2,2-Difluoro-ethylcarbamoyl)-ethyl]-carbamic acid tert-butyl ester

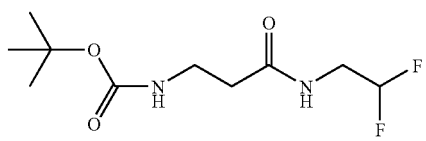

EDCI.HCl (3.86 g, 20.11 mmol, 1.3 eq.), HOBt (2.09 g, 15.47 mmol) and triethylamine (10.78 ml, 77.35 mmol, 5 eq.) was added to a solution of BOC-β-alaminol (2.93 g, 15.47 mmol) in dichloromethane (50 ml) and stirred at 0° C. for 15 mins. A solution of the fluoroamine (1 eq.) in dichloromethane (15 ml) was added and the mixture stirred at RT for 2 h. The mixture was washed with water (50 ml), the aqueous extracted with dichloromethane (2×50 ml), the combined organics dried (MgSO₄), filtered and evaporated to an oil, which was purified on by silica column chromatography to yield a colourless solid (2.76 g, 69%).

Intermediate 3b

[2-(2,2-Difluoro-ethylcarbamoyl)-ethyl]-carbamic acid

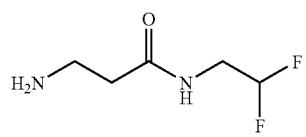

[2-(2,2-Difluoro-ethylcarbamoyl)-ethyl]-carbamic acid tert-butyl ester (2.75 g, 10.9 mmol) was suspended in 4M hydrochloric acid in dioxane (30 ml) and stirred at RT for 18 h. Dichloromethane was added (50 ml) and the solid filtered off and dried in vacuo (2.02 g, 100%).

Intermediates 4

The following syntheses are representative of the imidazole ethyl amines intermediates as shown in Scheme 2:

Intermediate 4a

{2-[1-(2-Fluoroethyl)-1H-imidazol-4-yl]-ethyl}-carbamic acid tert-butyl ester

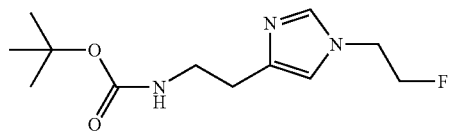

To a warmed (30° C.) suspension of 2-(2-fluoro-ethyl)-5-oxo-5,6,7,8-tetrahydro-imidazo[1,5-c]pyrimidin-2-ium (1.01 g, 3.82 mmol) in t-butanol (38 ml), was added Hunig's base (1.33 ml, 7.64 mmol) and the mixture heated to reflux under an inert atmosphere for 1.5 h. The mixture was cooled and the solvent evaporated to a yellow semi-solid, which was triterated with dichloromethane. The solid was filtered off and the filtrate purified by silica column chromatography, to yield a colourless solid (0.384 g, 39%).

Intermediate 4b

2-[1-(2-Fluoroethyl0-1H-imidazol-4-yl)-ethylamine triflate

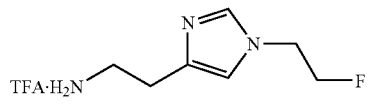

To a solution of {2-[1-(2-fluoroethyl)-1H-imidazol-4-yl]-ethyl}-carbamic acid tert-butyl ester (0.1 g, 0.389 mmol) in dichloromethane (5 ml), was added trifluoroacetic acid (1 ml) and stirred for 2 h. The solvent was evaporated and a solid triterated on addition of diethyl ether. This was used crude in the next step.

The invention claimed is:

1. A compound of formula I

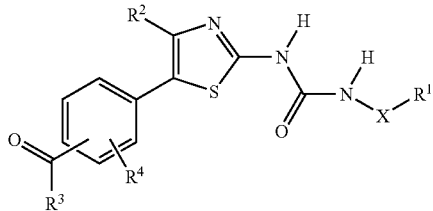

or a pharmaceutically acceptable salt thereof, wherein:

$R^1$ is $C_1$-$C_6$-alkylaminocarbonyl, where the alkyl is optionally substituted by one or more halo, hydroxyl or $C_1$-$C_6$-alkoxy groups, or $R^1$ is a 5- or 6-membered heteroaromatic ring having one or more ring heteroatoms selected from the group consisting of oxygen, nitrogen and sulphur, said ring, being optionally substituted by one or more halo, hydroxyl, $C_1$-$C_6$-alkyl or $C_1$-$C_6$-alkoxy groups, where said alkyl and alkoxy are optionally further substituted by one or more halo, hydroxyl or $C_1$-$C_6$-alkoxy groups;

$R^2$ is $C_1$-$C_3$-alkyl;

$R^3$ is $C_1$-$C_6$-alkyl, $C_3$-$C_6$-cycloalkyl, —$NR^5R^6$ or —$OR^7$, where said alkyl and cycloalkyl groups are optionally substituted by one or more halo, hydroxyl or $C_1$-$C_6$-alkoxy groups and said cycloalkyl group is optionally further substituted by $C_1$-$C_6$-alkyl;

$R^4$ is one or more optional phenyl substituents independently selected from halo, $C_1$-$C_6$-alkyl, hydroxyl or $C_1$-$C_6$-alkoxy, where said alkyl and alkoxy groups are optionally further substituted by one or more halo, hydroxyl and $C_1$-$C_6$-alkoxy groups; or $R^3$ and $R^4$ together form a fused 5-7 membered cycloalkanone ring;

$R^5$ and $R^6$ independently represent hydrogen, $C_1$-$C_6$-alkyl, $C_3$-$C_6$-cycloalkyl, hydroxyl or $C_1$-$C_6$-alkoxy, where said alkyl, alkoxy and cycloalkyl groups are optionally substituted by one or more halo, hydroxyl or $C_1$-$C_6$-alkoxy groups and said cycloalkyl group is optionally further substituted by $C_1$-$C_6$-alkyl;

$R^7$ is hydrogen, $C_1$-$C_6$-alkyl or $C_3$-$C_6$-cycloalkyl, where said alkyl and cycloalkyl groups are optionally substituted by one or more halo, hydroxyl or $C_1$-$C_6$-alkoxy groups and said cycloalkyl group is optionally further substituted by $C_1$-$C_6$-alkyl;

X is $CH_2$—$C(R^8)R^9$;

$R^8$ and $R^9$ are independently selected from hydrogen, halo, hydroxy and $C_1$-$C_6$-alkyl where said alkyl group is optionally substituted by one or more halo, hydroxyl or $C_1$-$C_6$-alkoxy groups; and the group $C(O)R^3$ is located at the 3- or 4-position on the phenyl ring.

2. A compound according to claim 1 where the group C(O)R3 is located at the 4-position on the phenyl ring.

3. A compound according to claim 1 where R1 is Ci-C-alkylaminocarbonyl, optionally substituted by one to three fluoro.

4. A compound according to claim 1 where R1 is optionally substituted imidazo-4-yl, 2H-tetrazol-5-yl or oxazol-2-yl.

5. A compound according to claim 1 where R2 is methyl.

6. A compound according to claim 1, where R3 is methyl, ethyl, cyclopropyl, methylamino, ethylamino, cyclopropylamino, hydroxyl or methoxy.

7. A compound according to claim 1, where X is ethylene.

8. A compound which is selected from:
3-{3-[5-(4-acetylphenyl)-4-methylthiazol-2-yl]-ureido}-N-tert-butylpropionamide;
3-{3-[5-(4-acetylphenyl)-4-methylthiazol-2-yl]-ureido}-N-(2-fluoroethyl)-propionamide;
3-{3-[5-(4-acetylphenyl)-4-methylthiazol-2-yl]-ureido}-N-(2,2-difluoroethyl)-propionamide;
3-{3-[5-(4-acetylphenyl)-4-methylthiazol-2-yl]-ureido}-N-(2,2,2-trifluoroethyl)-propionamide;
1-[5-(4-acetylphenyl)-4-methylthiazol-2-yl]-3-{2-[1-(2-fluoroethyl)-1H-imidazol-4-yl]-ethyl}-urea;
1-[5-(4-acetylphenyl)-4-methylthiazol-2-yl]-3-[2-(1-isopropyl-1H-imidazol-4-yl)-ethyl]-urea;
N-tert-butyl-3-{3-[(4-methyl-5-(4-propionylphenyl)-thiazol-2-yl]-ureido}-propionamide;
N-(2,2-Difluoroethyl)-3-{3-[4-methyl-5-(4-propionylphenyl)-thiazol-2-yl]-ureido}-propionamide;
1-{2-[1-(2-fluoroethyl)-1H-imidazol-4-yl]-ethyl}-3-[4-methyl-5-(4-propionylphenyl)-thiazol-2-yl]-urea;
3-{3-[5-(4-acetyl-3-fluorophenyl)-4-methylthiazol-2-yl]-ureido}-N-tert-butyl-propionamide;
3-{3-[5-(4-acetyl-3-fluorophenyl)-4-methylthiazol-2-yl]-ureido}-N-(2,2-difluoroethyl)-propionamide;
1-[5-(4-acetyl-3-fluorophenyl)-4-methylthiazol-2-yl]-3-[2-(1-isopropyl-1H-imidazol-4-yl)-ethyl]-urea;
N-(2,2-difluoroethyl)-3-{3-[4-methyl-5-(1-oxo-indan-5-yl)-thiazol-2-yl]-ureido}-propionamide;
1-{2-[1-(2-fluoroethyl)-1H-imidazol-4-yl]-ethyl}-3-[4-methyl-5-(1-oxo-indan-5-yl)-thiazol-2-yl]-urea;
1-[2-(1-isopropyl-1H-imidazol-4-yl)-ethyl]-3-[4-methyl-5-(1-oxo-indan-5-yl)-thiazol-2-yl]-urea;
N-tert-butyl-3-{3-[5-(4-cyclopropanecarbonylphenyl)-4-methylthiazol-2-yl]-ureido}-propionamide;
3-{3-[5-(4-cyclopropanecarbonyl-phenyl)-4-methylthiazol-2-yl]-ureido}-N-(2,2-difluoroethyl)-propionamide;
1-[5-(4-cyclopropanecarbonylphenyl)-4-methylthiazol-2-yl]-3-[2-(1-isopropyl-1H-imidazol-4-yl)-ethyl]-urea;
1-[5-(4-cyclopropanecarbonylphenyl)-4-methylthiazol-2-yl]-3-[2-(1-ethyl-1H-imidazol-4-yl)-ethyl]-urea;
1-[5-(4-cyclopropanecarbonyl-phenyl)-4-methylthiazol-2-yl]-3-{2-[1-(2-fluoroethyl)-1H-imidazol-4-yl]-ethyl}-urea;
1-[5-(4-cyclopropanecarbonylphenyl)-4-methylthiazol-2-yl]-3-[2-(2-ethyl-2H-tetrazol-5-yl)-ethyl]-urea;
1-[5-(4-cyclopropanecarbonylphenyl)-4-methylthiazol-2-yl]-3-[2-(5-ethyloxazol-2-yl)-ethyl]-urea;
4-{2-[3-(2-tert-butylcarbamoylethyl)-ureido]-4-methylthiazol-5-yl}-N-isopropyl-benzamide
4-(2-{3-[2-(2-fluoroethylcarbamoyl)-ethyl]-ureido)-4-methylthiazol-5-yl}-N-isopropyl-benzamide;
4-(2-{3-[2-(2,2-difluoroethylcarbamoyl)-ethyl]-ureido}-4-methylthiazol-5-yl)-N-isopropyl-benzamide;
N-isopropyl-4-(4-methyl-2-{3-[2-(2,2,2-trifluoroethylcarbamoyl)-ethyl]-ureido}-thiazol-5-yl-benzamide;
4-{2-[3-(2-tert-butylcarbamoylethyl)-ureido]-4-methylthiazol-5-yl}-N-cyclopropyl-benzamide;
N-cyclopropyl-4-(2-{3-[2-(2,2-difluoroethylcarbamoyl)-ethyl]-ureido}-4-methylthiazol-5-yl)-benzamide;
N-cyclopropyl-4-(2-{3-[2-(2-fluoroethylcarbamoyl)-ethyl]-ureido}-4-methylthiazol-5-yl)-benzamide;
N-cyclopropyl-4-(4-methyl-2-{3-[2-(2,2,2-trifluoroethylcarbamoyl)-ethyl]-ureido}-thiazol-5-yl)-benzamide;

4-{2-[3-(2-tert-butylcarbamoylethyl)-ureido]-4-methylthiazol-5-yl}-N-methyl-benzamide;
4-(2-{3-[2-(2,2-difluoroethylcarbamoyl)-ethyl]-ureido}-4-methylthiazol-5-yl)-N-methyl-benzamide;
N-cyclopropyl-3-(2-{3-[2-(2,2-difluoroethylcarbamoyl)-ethyl]-ureido}-4-methylthiazol-5-yl)-benzamide;
N-cyclopropyl-3-[2-(3-{2-[1-(2-fluoroethyl)-1H-imidazo-4-yl]-ethyl}-ureido)-4-methylthiazol-5-yl]-benzamide;
4-(2-{3-[2-(2,2-difluorethylcarbamoyl)-ethyl]-ureido}-4-methylthiazol-5-yl)-benzoic acid methyl ester;
4-(2-{3-[2-(1-isopropyl-1H-imidazol-4-yl)-ethyl]-ureido}-4-methylthiazol)-benzoic acid methyl ester;
4-[2-(3-{2-[1-(2-fluoroethyl)-1H-imidazol-4-yl]-ethyl}-ureido)-4-methylthiazol-5-yl]-benzoic acid methyl ester;
4-(2-{3-[2-(2,2-difluoroethylcarbamoyl)-ethyl]-ureido}-4-methylthiazol-5-yl)-benzoic acid ethyl ester;
4-[2-(3-{2-[1-(2-fluoroethyl)-1H-imidazol-4-yl]-ethyl}-ureido)-4-methylthiazol-5-yl]-benzoic acid ethyl ester;
4-(2-{3-[2-(2,2-difluorethylcarbamoyl)-ethyl]-ureido}-4-methylthiazol-5-yl)-benzoic acid;
4-(2-{3-[2-(1-isopropyl-1H-imidazol-4-yl)-ethyl]-ureido}-4-methylthiazol-5-yl)-benzoic acid;
4-[2-(3-{2-[1-(2-fluoroethyl)-1H-imidazol-4-yl]-ethyl}-ureido)-4-methylthiazol-5-yl]-benzoic acid;
4-{2-[3-(2-tert-butylcarbamoylethyl)-ureido]-4-methylthiazol-5-yl}-N-methoxy-N-methyl-benzamide;
4-(2-{3-[2-(1-isopropyl-1H-imidazol-4-yl)-ethyl]-ureido}-4-methylthiazol-5-yl)-N-methoxy-N-methyl-benzamide; and
4-[2-(3-{2-[1-(2-fluoroethyl)-1H-imidazol-4-yl]-ethyl}-ureido)-4-methylthiazol-5-yl]-N-methoxy-N-methyl-benzamide.

9. A pharmaceutical composition comprising a compound according to claim 1 and a suitable pharmaceutically acceptable excipient.

* * * * *